US012042650B2

(12) United States Patent
Ollivier

(10) Patent No.: US 12,042,650 B2
(45) Date of Patent: Jul. 23, 2024

(54) DUAL MULTIPOLAR LEAD IMPLANTABLE IN THE CORONARY VENOUS NETWORK

(71) Applicant: SORIN CRM SAS, Clamart (FR)

(72) Inventor: Jean-François Ollivier, Gif sur Yvette (FR)

(73) Assignee: SORIN CRM SAS, Clamart (FR)

( * ) Notice: Subject to any disclaimer, the term of this patent is extended or adjusted under 35 U.S.C. 154(b) by 750 days.

(21) Appl. No.: 17/170,424

(22) Filed: Feb. 8, 2021

(65) Prior Publication Data

US 2021/0236813 A1 Aug. 5, 2021

Related U.S. Application Data

(63) Continuation of application No. 16/302,051, filed as application No. PCT/EP2017/060661 on May 4, 2017, now Pat. No. 10,912,938.

(30) Foreign Application Priority Data

May 19, 2016 (FR) ...................................... 1654463

(51) Int. Cl.
*A61N 1/05* (2006.01)
*A61M 25/09* (2006.01)
*A61N 1/39* (2006.01)

(52) U.S. Cl.
CPC ........... *A61N 1/0563* (2013.01); *A61M 25/09* (2013.01); *A61N 1/056* (2013.01); *A61N 1/0565* (2013.01);
(Continued)

(58) Field of Classification Search
CPC .... A61N 1/0563; A61N 1/056; A61N 1/0565; A61N 1/3918; A61N 2001/0585; A61M 25/09
See application file for complete search history.

(56) References Cited

U.S. PATENT DOCUMENTS 5,144,960 A 9/1992 Mehra et al.
6,772,015 B2 8/2004 Dahl et al.
(Continued)

FOREIGN PATENT DOCUMENTS

EP 0 993 840 A1 4/2000
EP 1 938 861 A1 7/2008
(Continued)

OTHER PUBLICATIONS

International Search Report and Written Opinion on International Patent Application No. PCT/EP2017/060661 dated Jun. 26, 2017. 10 pages.

*Primary Examiner* — Amanda K Hulbert
*Assistant Examiner* — Philip C Edwards

(57) ABSTRACT

The disclosure relates to a multipolar, detection/stimulation endovascular lead intended to be implanted in the coronary venous network. The lead comprises a lead body with in proximal portion a connector to a cardiac pacemaker/defibrillator generator, and in a distal portion a first branch and a second branch extending beyond a bifurcation. The distal ends of the branches are free ends carrying an array of electrodes connected to the connector. Each of the branches comprises at its free end an outlet in the distal direction, able to receive an implantation guide wire inserted therein and to guide the implantation guide wire in an axial direction parallel to the main axis of the lead body.

19 Claims, 3 Drawing Sheets

(52) U.S. Cl.
CPC .... *A61N 2001/0585* (2013.01); *A61N 1/3918* (2013.01)

(56) References Cited

U.S. PATENT DOCUMENTS

| | | |
|---|---|---|
| 2002/0111675 A1 | 8/2002 | Wilson |
| 2006/0259084 A1 | 11/2006 | Zhang et al. |
| 2009/0062898 A1 | 3/2009 | Das |
| 2009/0118701 A1* | 5/2009 | Nimkar ................ A61M 25/09 604/509 |
| 2009/0248111 A1* | 10/2009 | Pianca ................... A61N 1/05 607/116 |
| 2010/0057020 A1 | 3/2010 | Uretsky |
| 2011/0257709 A1 | 10/2011 | Ackermann et al. |

FOREIGN PATENT DOCUMENTS

| | | | |
|---|---|---|---|
| EP | 2 455 131 | A1 | 5/2012 |
| EP | 2 559 453 | A1 | 2/2013 |
| EP | 2 572 751 | A1 | 3/2013 |
| EP | 2 581 107 | A1 | 4/2013 |
| EP | 2 719 422 | A1 | 4/2014 |
| EP | 2 959 828 | A1 | 12/2015 |
| FR | 2756173 | A1 | 5/1998 |
| FR | 2993771 | A1 | 1/2014 |

\* cited by examiner

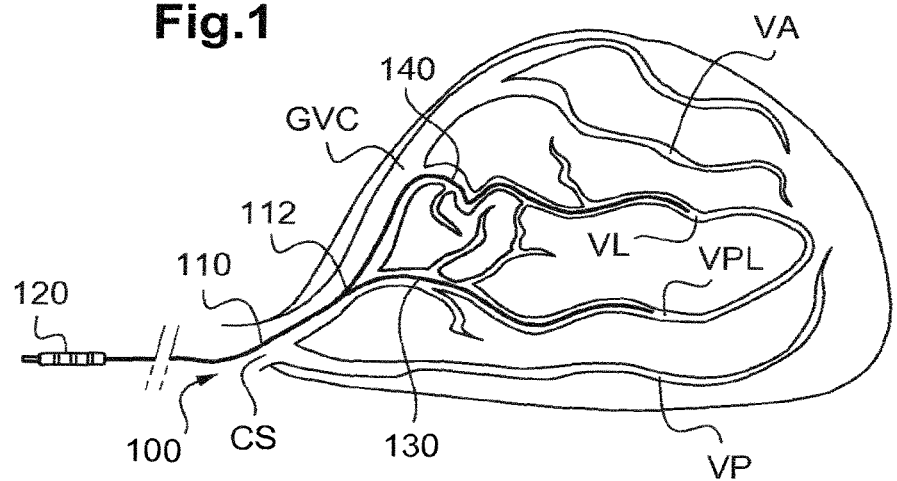
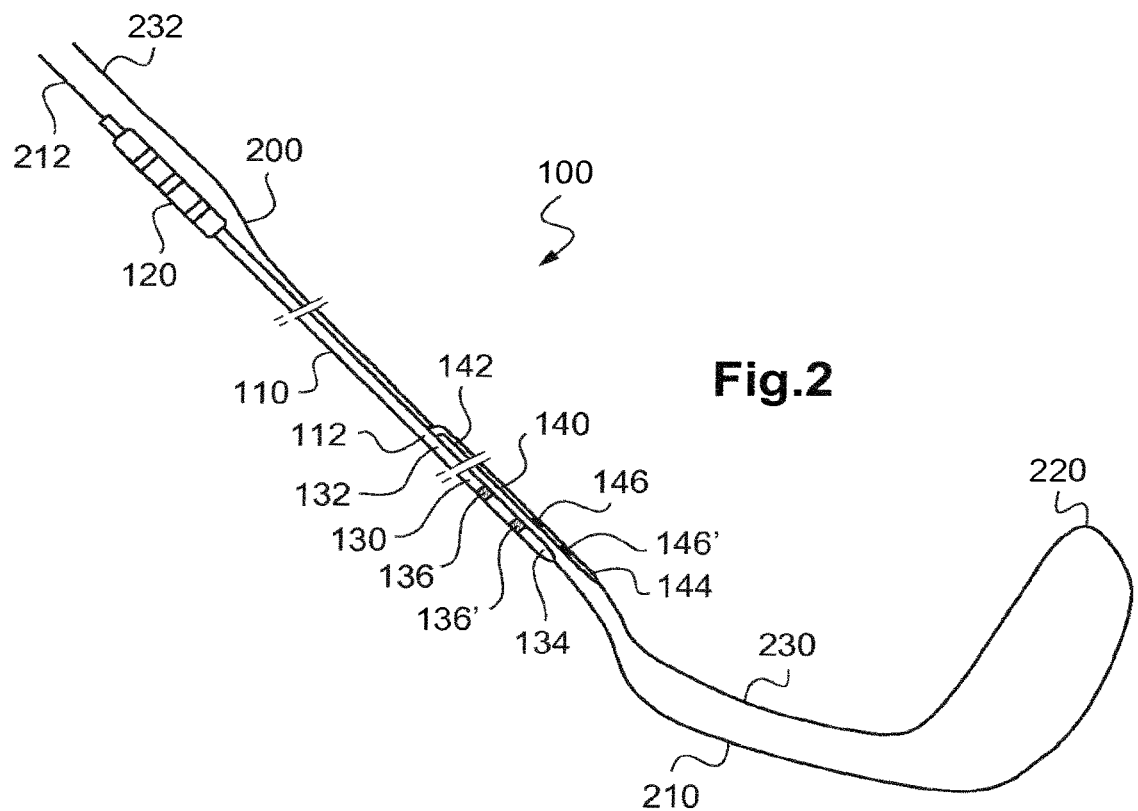

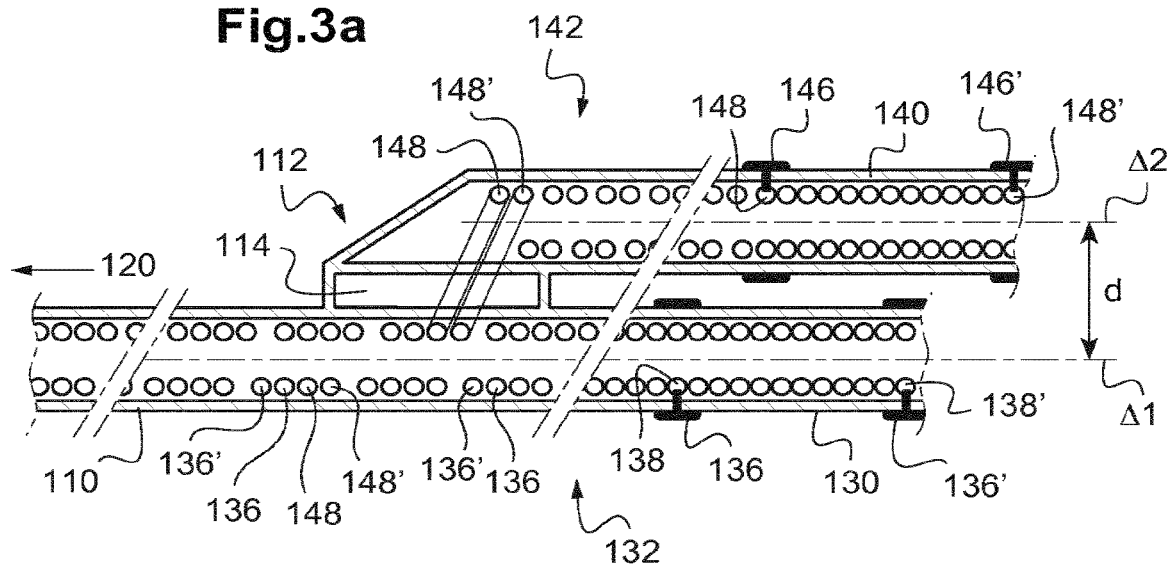
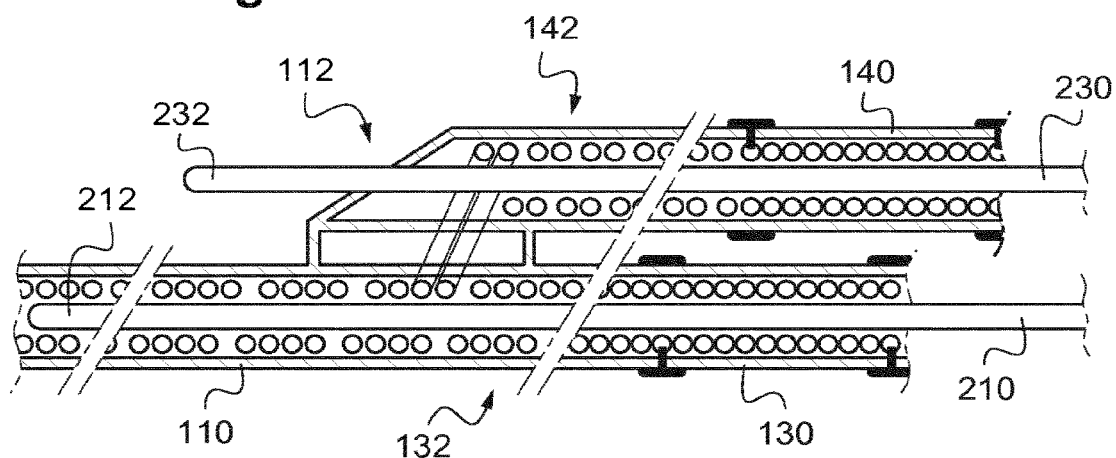

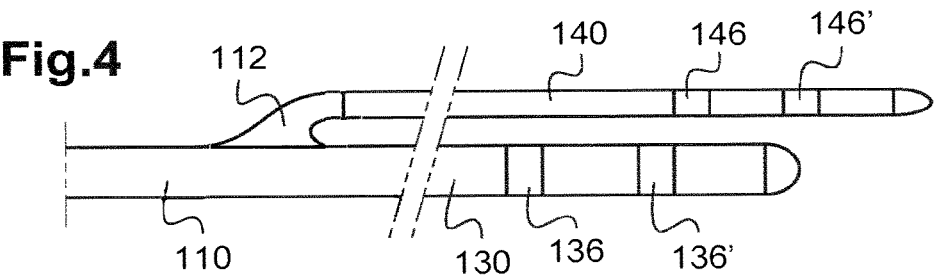
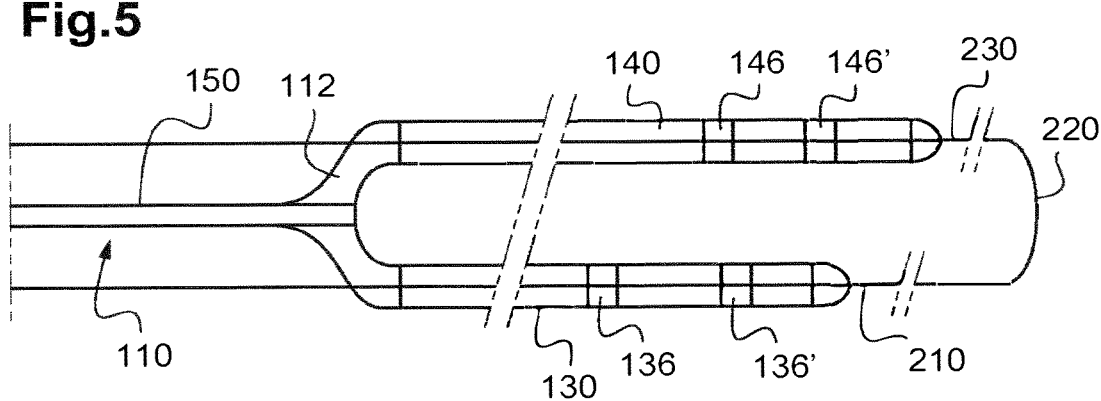
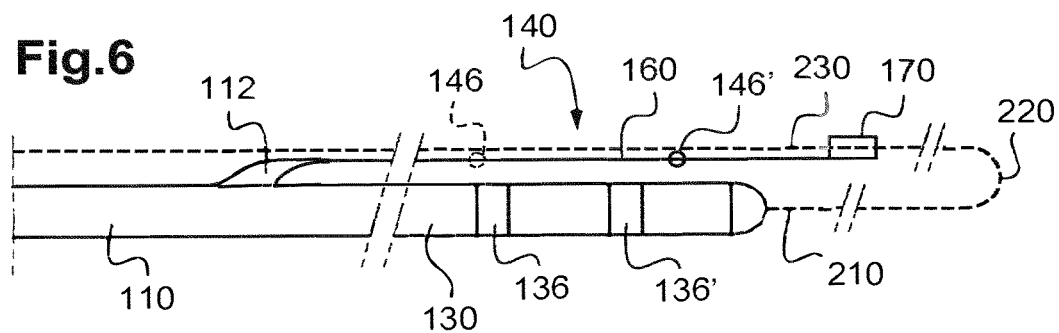
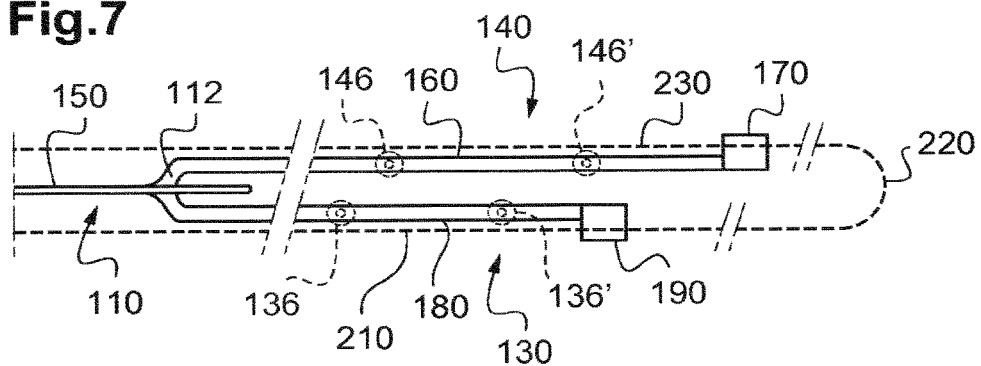

DUAL MULTIPOLAR LEAD IMPLANTABLE IN THE CORONARY VENOUS NETWORK

CROSS-REFERENCE TO RELATED PATENT APPLICATIONS

This application is a continuation of U.S. application Ser. No. 16/302,051, filed Nov. 15, 2018, which is a 371 U.S. National Stage Application of International Application No. PCT/EP2017/060661, filed May 4, 2017, which claims the benefit of and priority to French Patent Application No. 1654463, filed May 19, 2016, all of which are incorporated herein by reference in their entireties.

BACKGROUND

The invention relates to "active implantable medical devices" as defined by the Directive 90/385/EEC of 20 Jun. 1990 of the Council of the European Communities, more precisely implants for continuously monitoring the heart rate and delivering, if necessary, to the heart Electrical pulses for stimulation, resynchronization and/or defibrillation in the event of a rhythm disorder detected by the device.

It relates more specifically to detection/stimulation endovascular cardiac leads intended to be implanted in the coronary artery of the heart to allow the stimulation of a left, ventricle or atrium, cavity and/or the detection of depolarization potentials at these cavities.

Unlike right cavities for which it is sufficient to implant endocardial leads via the right peripheral venous network, placing permanent leads in a left heart cavity would involve significant operational risks, for example the risk of bubbles to the cerebral vascular network located downstream of the left ventricle.

For this reason, for the detection/stimulation of a left cavity, it is generally chosen to introduce a lead not into the cavity to be stimulated but into the coronary artery, the lead being provided with an electrode which is applied against the cavity wall of the epicardium and directed towards the left ventricle or the left atrium, as the case may be. These leads stimulate the cardiac muscle via one or more point electrodes whose position is a function of the predefined trajectory of the cannulated vein.

A lead of this type is, for example, the Situs LV model, marketed by Sorin CRM (Clamart, France) and described in EP 0 993 840 A1 (ELA Medical).

The introduction of such an endovascular lead is made by the coronary sinus, from its outlet into the right atrium. The lead is then pushed and oriented along the network of coronary veins to the chosen site. This procedure is very delicate given the particularities of the venous network and its access routes, including the passage of valves and tortuosities as well as the gradual decrease in diameter of the duct as the lead progresses in the selected coronary vein. Once the target vein has been reached, the surgeon seeks a satisfactory stimulation site, with good electrical contact of the stimulation electrode against the tissue of the epicardium, this contact having to be maintained despite various variations or stresses over time.

Furthermore, it has been proposed to arrange several electrodes along the lead body to increase the chances of an acceptable compromise, possibly giving the lead body a particular conformation.

The surgeon can thus select from among the various electrodes present on the lead body the one that provides the best efficiency on the electrical and hemodynamic points of view. Such a multi-electrode lead is described in particular in EP 1 938 861 A1 (ELA Medical).

It has also been proposed to widen the stimulation zone in order to stimulate several regions of the epicardium, in particular by stimulating concomitantly two relatively distant zones, located in two distinct veins. The double effect of moving these two zones and multiplying the stimulation points in each of the zones provides a particularly beneficial effect, in particular for resynchronizing the operation of the heart. In general, multiple multipoint stimulation (MPP) of the left ventricle has many advantages, and this approach is made possible by the availability of multipolar left ventricular leads, which allow for wider triggering of cardiac cells, leading in particular to better contractility.

If this approach is interesting, its implementation via a monobody lead nevertheless has an intrinsic limitation: the distance between the stimulation points is relatively small, especially since the most distal electrode is often unusable because of undesirable phrenic stimulation (stimulation occurring due to the apical positioning of the most distal electrode). In fact, the useful distance between the two stimulation points of a single-body lead is less than 30 mm, for typical curvilinear lengths of the left ventricle of the order of 80 mm in the mitral valve/apex axis and 70 mm for the basal circumference.

To remedy this difficulty, a first proposal consists in implanting two standard ventricular leads of the standard type, these leads being coupled proximally by means of a standardized Y-adapter IS-1 or IS-4, or at the level of the pulse generator by means of a housing head adapted to receive separately the respective connectors of the two left ventricular leads.

Another proposal consists in implementing not endovascular leads but epicardial leads, implanted surgically or mini-surgically. However, this technique is very rarely used because it is too invasive for a benefit that is still uncertain.

In order to avoid having to concurrently implant two separate leads in the coronary venous network, which is technically very difficult. US 2002/143380 A1 (U.S. Pat. No. 6,772,015 B2) proposes to produce a single endovascular lead comprising a lead body equipped with a defibrillation coil and having, upstream of the coil, a branch from which a lateral extension intended to penetrate into a secondary vessel extends. The resulting configuration is that of a bifurcation between a "finger portion" (the elongated main lead body extending beyond the bifurcation) and a "thumb portion" (the short side branch). The insertion of this lead is effected by prior insertion of the two parts together in a catheter of suitable diameter. The catheter is then advanced into the main vein of the coronary artery up to the level of the secondary vessel. The lead is then pushed out of the catheter so that the finger portion advances in the main vein and then, as the thumb portion reaches the outlet of the catheter, that thumb portion is directed toward the secondary vessel to be progressively introduced therein at the same time that the finger portion finishes its progression in the main vein. The catheter is finally removed when the lead with its two branches reaches its definitive final position.

However, this device requires considerable skill from the practitioner for the correct insertion of the thumb portion into the secondary vessel.

Moreover, this thumb portion is of very short length, and provides only a very punctual stimulation, which is also confined to the region near the outlet of the secondary vessel in the main vein. Finally, the use of a catheter with a relatively large diameter (it must be able to accommodate the two branches of the lead side by side in its internal lumen) precludes the possibility of intervention in deep regions of the coronary venous network, which are yet the most favorable regions in terms of effectiveness of stimulation of the left cavities of the heart.

Another technique is proposed by EP 2,559,453 A1 and EP 2 572 751 A1 (Sorin CRM), which consists in introducing the distal part of the lead down a first vein ("outward" vein) and then by an anastomosis towards a second vein ("return" vein) by going back up into it. Indeed, the presence of distal anastomoses in the coronary venous network has been observed in a large proportion of patients, i.e. at the end of some veins there is a passage to another vein, which makes possible communication between two distinct veins at the level of the anastomosis, via their respective distal ends.

The distribution of the electrodes on the lead may be chosen such that these electrodes are grouped into two separate sets forming two distinct active parts, one intended to stimulate in the outward vein and the other in the return vein. These two groups of electrodes are separated by an electrode-free region corresponding to the most distal part of the outward vein, the region of the anastomosis and to the most distal part of the return vein.

This technique implies, however, that not only the anastomosis is present but it is sufficiently wide to be able to introduce the lead body there and then to advance the latter during the upward phase in the return vein.

SUMMARY

The object of the present invention is to propose a novel bifurcated endovascular lead configuration, i.e. a single lead having two branches in its distal part, which overcomes the disadvantages of the leads proposed up to now, by providing the following benefits:
  long length of the two branches, allowing a large distance between the stimulation points, and consequently a greater extent of the stimulated region of the myocardium (multipoint and multivein stimulation);
  compatibility with standard generator housings, with a single connector on the proximal side, for example a IS-4 standardized connector;
  ease of implantation, the lead using only conventional techniques very well mastered by the practitioners, and standard implantation accessories (guidewire, guide-catheter, sub-selection catheter, etc.);
  reliability over time;
  Stability of positioning of the lead once implanted in the venous network;
  possibility of extraction in case of necessity;
  ease of industrialization, the realization of the lead using only conventional, proven techniques.

To this end, the invention provides a multipolar detection/stimulation endovascular lead comprising, in a manner known per se: a lead body; in the proximal part of the lead body, a connector for connection to a cardiac pacemaker/defibrillator generator; and in the distal part of the lead body, an active portion extending the lead body beyond a bifurcation of the lead body from which a first branch and a second branch extend. The proximal ends of the first and second branches are joined at the bifurcation and the distal ends of the first and second branches are free ends and each of the first and second branches carries an array of electrodes connected to the connector.

Typically, this lead being intended to be implanted by wire-guiding, each of the first and second branches comprises a distal guide element presenting at the free end of the branch an outlet in the distal direction, this outlet being capable of receiving an implantation guide wire inserted therein and guiding this implantation guide wire in an axial direction parallel to the main axis of the lead body.

According to various embodiments of the invention, and various advantageous subsidiary characteristics:
  The distal guiding element of the first and/or the second branch is formed by a hollow sheath forming a body of the branch and traversed right through by a central lumen extending from the outlet at the free end of the branch to an outlet at the opposite proximal end situated in the vicinity of the bifurcation, the central lumen being adapted to receive the implantation guide wire inserted therein and the opening at the opposite proximal end being capable of guiding this implantation guide wire in an axial direction parallel to the main axis of the lead body and radially at a distance from the lead body;
  The distal guiding element of the first and/or the second branch is a hollow guiding nacelle mounted in the vicinity of the free end of the branch, this hollow guiding nacelle being able to receive the implantation guide wire introduced therein and guiding this implantation guide wire in an axial direction parallel to the main axis of the lead body and radially away from the lead body;
  The lead body is formed by a hollow sleeve through which a central lumen passes.
  One of the branches then being advantageously formed by an axial extension of the lead body, the distal guiding element of the branch being formed by a hollow sheath through which a central lumen communicating with and extending the central lumen of the lead body at the bifurcation passes, the lumens of the lead body and of the branch being adapted together to receive the implantation guide wire inserted therein;
  The lead body is formed by a microcable extending from the connector at the bifurcation and carrying at the bifurcation a supporting and connecting element of the first and second branches;
  The first and/or the second branch is formed by a microcable extending from the bifurcation at the free end of the branch, the lead body carrying at the level of the bifurcation a supporting and connecting element of the first and/or second branch;
  The respective electrode arrays of the first and second branches are electrically distinct arrays separately connected to respective poles of the connector by a common multipolar conductive arrangement of the lead body.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which:

FIG. 1 generally illustrates the myocardium, with the main veins of the coronary artery network in which a lead according to the invention has been implanted, intended for stimulation of the left ventricle.

FIG. 2 is an overall view of the lead according to the invention, showing the various elements which constitute it and the guide wire used for its implantation.

FIGS. 3*a* and 3*b* are detailed views, in section, of the lead of the invention at the level of the branch, respectively, without and with the insertion guide wire inserted in the lumens of the two branches of the lead.

FIGS. 4 to 7 illustrate lead configurations corresponding to various embodiments of the invention.

DETAILED DESCRIPTION

Embodiments of the lead according to the invention will now be described.

FIG. 1 generally illustrates the myocardium and the main vessels of the coronary artery network, in which a lead 100 has been introduced in order to stimulate the left ventricle.

This lead 100 is endocardially implanted into the coronary venous network via the superior vena cava, the right atrium and the CS entrance of the venous coronary sinus. The coronary venous network then develops in several branches from the large coronary vein GVC, these branches comprising the posterolateral VPL, lateral VL, anterolateral VA and posterior VP veins.

FIG. 2 illustrates more precisely the various constituent elements of the endovascular lead 100 of the invention, implanted in the coronary artery as illustrated in FIG. 1.

This lead 100 comprises a lead body formed, in the illustrated example, of a flexible hollow sheath with an internal lumen. This lead body has a bifurcation 112 on the distal side and a connector 120 for connection to the connector head of a pacing pulse generator, for example IS-4 standard connector.

From the bifurcation 112 two branches 130, 140 extend. In this embodiment, the first branch 130 is constituted by a hollow sheath with an internal lumen which extends axially the lead body 110 on the proximal side. The distal end 134 of the branch 130 is a free end with a through opening, preferably provided with a shutter allowing only the sealing passage of a tip 210 of a loop 220 of a guide-wire 200 for the implantation procedure which will be described below. The branch 130 is also provided with one or more electrodes, with in the illustrated example two electrodes 136, 136' connected respectively to two distinct poles of the connector 120 via connection conductors which will be described in more detail with reference In FIG. 3*a*.

The second branch 140 is connected at its proximal end 142 to the bifurcation 112 of the lead body and extends in a direction generally parallel to the lead body 110 and to the first branch 130 in the vicinity of the branch 130 at a substantially constant distance from the latter. In the described embodiment, the branch 140 is formed of a hollow sheath with an internal lumen opening out on the side of the proximal end 142 as well as on the side of the distal end 144, preferably with a shutter allowing only the passage of a return end 230 of the loop 220 of the guide wire 200 used for the implantation procedure. The branch 140 is provided with one or more electrodes, in the example illustrated, two electrodes 146, 146', connected to separate poles of the connector 120.

The connector 120 may in particular be a standardized quadripolar IS-4 connector, the respective poles of which are connected to the four electrodes 136, 136', 146 and 146'.

The typical length of the branches 130, 140 is of the order of 30 to 100 mm, the branches being of different lengths.

Furthermore, one or the other of these branches 130 and 140, or both branches, may be pre-formed, for example bent in a distal part, to ensure better retention in the vascular network and/or better contact of the electrodes with the tissues, according to techniques known per se.

Moreover, as illustrated in FIG. 2, it may be advantageous to provide an offset of the distal ends 134, 144 of the two branches 130, 140, on the order of 5 to 50 mm, in order to facilitate intravenous progression.

With regard to the electrodes, the electrode 136 (and/or 136'), and likewise the electrode 146 (and/or the electrode 146'), may consist of an isopotential electrode doublet, the two electrodes of the doublet being situated on the same branch, or on either branch.

The configuration of the various elements of the lead 100 allows the introduction into each of the two branches of a single implantation guide wire 200 with a first portion or end portion 210 extending inside the lead body 110 and of the first branch 130, opening at the end 134 of this branch 130, in order to form a loop 220 continuing in a second part or return end 230 which penetrates into the distal end 144 of the second branch 140, to the proximal end 142 from which it opens outwardly.

The guide wire 200 is thus presented to the practitioner in its most proximal part with two ends 212, 232. The part corresponding to the end 212 (the end piece 210) passes axially through the connector 120 and the lead body 110, while the part corresponding to the end 232 (return end 230) joins the second branch 140.

FIGS. 3*a* and 3*b* are detailed views in section at the bifurcation 112, respectively, without and with the forward end 210 and the return end 230 of the guide wire 200 inserted in the branches 130, 140.

The two proximal ends 132, 142 of the branches 130, 140 are joined at the bifurcation 112, so that the internal lumens and hollow sheaths forming the two branches 130, 140 extend along substantially parallel directions A1 and A2 between them and with a spacing d in the transverse direction. The two sheaths of the branches 130, 140 are joined together at the bifurcation 112 by a flexible bridge 114. The distal end 142 of the branch 140 opens out in the distal direction so as to allow passage of the return end 230 of the guide wire 200, as illustrated in FIG. 3*b*.

The two branches 130, 140 thus ensure the guiding and the parallelism of the two ends of the guide wire once these two ends have been introduced into the internal lumens of the branches wherein they are guided.

The independent electrodes 136, 136' of the branch 130 are connected to respective insulated wires 138, 138', and likewise the independent electrodes 146, 146' of the branch 140 are connected to respective insulated wires 148, 148'.

These insulated wires are wound inside each of the branches 130, 140 so as to leave the central lumen free to allow insertion of the guide wire ends 210, 230. The respective wire groups 138, 138' and 148, 148' are then gathered at bifurcation 112 into a bundle of four wires 136, 136', 146, 146' wound along the length of the lead body to the connector 120, the four poles of which are connected to each of the respective conductors.

The implantation of the lead of the invention is carried out by the following steps (all of which implement conventional techniques, very well mastered by the practitioners):

Establishing an access to the coronary sinus by an implantation catheter;

Introduction of the implantation guide wire 200 into a loop technique via an anastomosis of the coronary artery, a technique known per se (retrograde insertion);

Once the loop guide wire is put in place, cutting the guide catheter and inserting the two lead branches 130, 140 onto the two ends of the guide wire emerging on the proximal side. The lead is then progressively introduced into the venous network and pushed to the target zones selected in the preceding step;

Once the lead has reached its final location, removal of the guide wire.

Various variations or improvements of this implantation technique can be envisaged.

In particular, the design of the lead according to the invention makes it possible to use an additional accessory making it possible to increase very substantially the "pushability" (the progression ability of the lead in the venous network by an action exerted from the proximal end accessible to the practitioner). Indeed, it is possible to thread on the end 232 of the guide wire passing through the second branch 140 (guiding the "return" end 230 of the guidewire) a conventional guide catheter of diameter 4 or 5 French (33 mm or 1.66 mm) abutting the bifurcation 112, thus in a region of the lead very close to its most distal part.

Since the "pushability" properties of such a temporary guide catheter are very substantially superior to those of a conventional lead body, the push will be particularly effective. Moreover, contrary to a conventional left ventricular pacing lead, the risks of damage to the lead body due to the high stresses exerted during insertion of the lead (push and torsion maneuver) are significantly reduced: indeed, the stresses mainly pass through the temporary guide catheter, which is removed at the end of the operation.

Alternatively, it is possible to temporarily connect in rotation the end of the temporary guide catheter and the proximal end of the lateral branch 140 of the lead in order to apply slight angular movements to promote the progression of the assembly.

In one variant embodiment, it is possible to use two independent guide wires pushed far into the target veins, in order to avoid the stresses associated with the passage of an anastomosis and the recapture of the distal end of the "return" end 230 of the guide wire to form the loop 220.

FIGS. 4 to 7 illustrate lead configurations corresponding to various embodiments of the invention.

FIG. 4 illustrates the configuration described above with reference to FIGS. 2, 3a and 3b, wherein the lead body 110, the first branch 130 and the second branch 140 are all made in the form of a hollow sheath with a central lumen.

The first branch 130 extends in the extension of the lead body 110, while the second branch 140 is a lateral branch extending parallel to the branch 130 and connected to the outer surface of the sheath of the lead body 110 at the bifurcation 112.

FIG. 5 illustrates a variant wherein the lead body consists of a multipolar microcable 150, hence without central lumen.

The two branches 130, 140 extend parallel to one another and are connected to the distal end of the microcable 140 by the bifurcation 112, the two branches 130, 140 having a structure comparable to that described for the branch 140 of the embodiment of FIGS. 2 to 4.

Essentially, a microcable consists of an assembly, for example a strand of several cables of very small diameter, each comprising an electrically conductive core provided with an insulating coating.

The specific structure of the microcable may in particular be that described in EP 2 455 131 A1 and EP 2 581 107 A1 (Sorin CRM), to which reference may be made for further details.

The method of implantation of the lead illustrated in FIG. 5 will now be considered.

The design of this embodiment of the lead makes it possible to use one or two additional accessories making it possible to increase very substantially the "pushability", that is to say the progression ability of the lead in the venous network by an action exerted from the proximal end accessible to the practitioner.

Indeed, it is possible to thread on one or both ends 212 and 232 of the guide wire passing through the two branches 130 and 140 a single guide catheter or two separate guide catheters on each guide wire, this (these) catheter(s) being per se conventional, typically having a diameter of 4 or 5 French (1.33 mm or 1.66 mm) abutting the bifurcation 112, thus in a region of the lead very close to its most distal part. This variant of implantation including two guide catheters is possible because of the very small diameter of the body 150 made of microcable. Since the "pushability" properties of such a temporary guide catheter are very substantially superior to those of a conventional lead body, the push is particularly effective. Moreover, contrary to a conventional left ventricular pacing lead, the risks of damage to the lead body due to the high stresses exerted during insertion of the lead (push and torsion maneuver) are substantially reduced: indeed, the stresses mainly pass through the temporary guide catheter, which is removed at the end of the operation.

In a variant, it is possible to temporarily bind the end of the temporary guide catheter and the proximal end of one or more branches 130 and 140 of the lead in order to apply slight angular movements to promote the progression of the catheter assembly.

In another variant of implementation, it is possible to use two independent guide wires pushed very far into the target veins, in order to avoid the stresses associated with the passage of an anastomosis and the recapture of the end of the distal end of the "return" end 230 of the guidewire to form the loop 220.

FIG. 6 illustrates another embodiment of the invention wherein the lead body 110 and the first branch 130 have the same configuration as in the embodiment of FIGS. 2 to 4, that is to say they consist of a hollow sheath with the branch 130 in the extension of the lead body 110. On the other hand, the second branch 140 is made in the form of a monopolar or multipolar microcable 160.

To ensure guiding of the return end 230 of the guidewire, a guiding element 170 is provided at the distal end of the branch 140 in the form of a Rapid Exchange type ring or nacelle enabling this branch 140 (i.e. the microcable 160) to be guided to the selected target vein.

The microcable 160 may advantageously consist of a conductive core provided with an insulating coating, with the exception of punctually exposed areas used to constitute the detection/stimulation electrodes 146, 146'.

This makes it possible, as described in EP 2 719 422 A1 (Sorin CRM), to have a plurality of electrically independent conductors assembled together, for example stranded, so as to obtain an element provided with several distinctly selectable electrodes. The specific structure of the microcable can in particular be that described in the aforementioned EP 2 455 131 A1 and EP 2 581 107 A1 (Sorin CRM), to which reference may be made for further details. The very small diameter of the microcable 160 makes it possible in particular to exploit the entire length of the vein and cannulate vessels of very small diameter, which makes it possible to operate in new regions that are difficult to reach and thus to optimally use all the veins present in the basal zone, in particular to avoid the risk of phrenic stimulation, which generally increases when the lead is too distal.

The implantation method is as follows:

Access to the coronary sinus by an implantation catheter;

Introduction of the implantation guide wire 200 using a loop technique via an anastomosis of the coronary artery, a technique known per se (retrograde insertion);

Once the loop guide wire has been put in place, possible cut-out (the dimensions of the system remain compatible with the central lumen of the implantation catheter-guide) of the guide catheter and insertion of one end of the guide wire into the branch 130, then insertion of the other end of the guide wire into the nacelle 170. The lead is then progressively introduced into the venous network and pushed to the target zones selected in the preceding step;

Once the lead has reached its final location, removal of the guide wire.

The use of a guide catheter on the guide wire leading to the nacelle is preferable for the reasons already described above and due to the relative flexibility of the microcable branch. It should be noted that in this case the push point is at the most distal end of the branch and therefore very effective.

FIG. 7 illustrates yet another embodiment of the lead of the invention, wherein one and the other branch 130, 140 are each constituted by a microcable, respectively, 160 or 180, like the microcable 160 of the embodiment of FIG. 6. Each of the microcables 160, 180 is provided with a respective guiding element in the form of a nacelle 170, 190 to guide the return end 230 and the guide wire end 210 respectively.

The method of implantation is then as follows:

Establishing an access to the coronary sinus by an implantation catheter;

Introduction of the implantation guide wire 200 with a loop technique via an anastomosis of the coronary artery, a technique known per se (retrograde insertion);

Once the loop guide wire has been put in place, possible cutout (the dimensions of the system remain compatible with the central lumen of the implantation catheter-guide) of the guide catheter and insertion of one end of the guide wire into the nacelle 190, then insertion of the other end of the guide wire into the nacelle 170. The lead is then progressively introduced into the venous network and pushed to the target zones selected in the preceding step;

Once the lead has reached its final location, removal of the guide wire.

The use of one or two separate guide-catheter(s) on each guide wire leading to the nacelle is also conceivable for the reasons already described above.

Various variations of the embodiments described above can be envisaged.

It is thus possible to provide a lead comprising three or more branches formed on the same principle, by adding an additional branch to the two branches 130, 140 extending from the bifurcation 112.

Still another variant consists in providing one of the branches of a defibrillation coil for the possible application to the myocardium of a high energy shock at a left cavity.

A further alternative embodiment consists in providing a lead body 110 in the form of a tubular sheath, the diameter of the internal lumen of which makes it possible to accommodate the two forward 210 and return 230 ends of the guide wire 200 or a lead body comprising two distinct internal lumens, for the same purpose. This makes it possible to optimize the trajectories of the two ends of the guidewire and the good sliding of the lead on the guidewire while avoiding potential kinks of the two ends of the guidewire.

Still another improvement is to provide the distal ends of the two branches 130, 140 with a mechanical connection system, for example of the male cone/female cone type or a bayonet system, making it possible to make a loop formed by these two branches in the venous network. This makes it possible, by design, to ensure perfect stability of the lead in the coronary venous network after its implantation, the loop branches being locked distally in the venous network.

What is claimed is:

1. A lead for implantation in a coronary venous network, the lead comprising:
    a lead body extending from a proximal end of the lead to a bifurcation at a distal end of the lead body;
    a first branch extending from the bifurcation and comprising a first set of electrodes and a first guiding element that includes a first opening at a distal end of the first branch, wherein the first set of electrodes is positioned on an outer surface of the first branch; and
    a second branch extending from the bifurcation and comprising: i) a second set of electrodes positioned on an outer surface of the second branch, ii) a second opening at a proximal end of the second branch, and iii) a second guiding element that includes a third opening at a distal end of the second branch, wherein the second branch is formed by a hollow sleeve with an internal lumen that extends from the second opening to the third opening; and
    wherein the first guiding element and the second guiding element are configured to receive an implantation guide-wire and guide the implantation guide-wire in an axial direction parallel to a main axis of the lead body.

2. The lead of claim 1, wherein the second guiding element is formed by the hollow sleeve of the second branch, the internal lumen of the second branch configured to receive the implantation guide-wire inserted therein, and the second opening configured to guide the implantation guide-wire in the axial direction parallel to the main axis of the lead body and radially at a distance from the lead body.

3. The lead of claim 1, wherein at least one of the first guiding element or the second guiding element are a hollow guiding nacelle configured to receive the implantation guide-wire therein and to guide the implantation guide-wire in the axial direction parallel to the main axis of the lead body and radially at a distance from the lead body.

4. The lead of claim 1, wherein the lead body is formed by a hollow sheath crossed from side to side by a central lumen.

5. The lead of claim 1, wherein one of the first branch or the second branch is formed by an axial extension of the lead body, the first or second guiding element of the corresponding branch being formed by a hollow sleeve crossed from side to side by a central lumen of the lead body at the bifurcation, the central lumen of the lead body and an internal of the corresponding branch being adapted to receive the guide-wire inserted therein.

6. The lead of claim 1, wherein the lead body comprises a microcable extending from a connector positioned at the proximal end of the lead body to the bifurcation.

7. The lead of claim 1, wherein at least one of the first branch or the second branch is formed by a microcable extending from the bifurcation to the distal end of the corresponding branch.

8. The lead of claim 7, wherein the microcable comprises one or more punctually exposed areas that form the first set of electrodes or the second set of electrodes.

9. The lead of claim 1, wherein the bifurcation comprises a flexible bridge that couples the first branch and the second branch.

10. The lead of claim 1, wherein the first set of electrodes and the second set of electrodes are electrically distinct arrays separately connected to respective poles of a connector by a common multipolar conducting arrangement of the lead body, the connector positioned at the proximal end of the lead body and configured to couple the lead to a cardiac pacemaker/defibrillator generator.

11. The lead of claim 1, wherein at least one of the first opening or the second opening comprise a shutter for sealing the at least one of the first opening or the second opening.

12. The lead of claim 1, further comprising one or more insulated wires wound inside at least one of the first branch or the second branch, wherein the one or more insulated wires are wound to maintain an open central lumen of the first branch or the second branch for allowing insertion of the guide-wire.

13. The lead of claim 12, wherein the first set of electrodes and the second set of electrodes are electrically coupled to respective wires of the one or more insulated wires.

14. The lead of claim 1, wherein the first branch is an extension of the lead body, and wherein the second branch is a lateral branch extending parallel to the first branch.

15. The lead of claim 1, further comprising a connector positioned at the proximal end of the lead body and structured to couple the lead to a cardiac pacemaker/defibrillator generator.

16. The lead of claim 15, wherein the connector is a quadripolar IS-4 connector.

17. The lead of claim 1, wherein the first branch and the second branch are different lengths.

18. The lead of claim 1, wherein the first branch the second branch are between 30 mm and 100 mm in length.

19. The lead of claim 1, wherein the distal end the first branch and the distal end of the second branch are offset between 5 mm and 50 mm.

* * * * *